United States Patent [19]

Regnat et al.

[11] Patent Number: 5,281,640

[45] Date of Patent: Jan. 25, 1994

[54] DIARYLPHOSPHINOUS ACID ARYL ESTERS, A PROCESS FOR THEIR PREPARATION AND THEIR USE FOR STABILIZING PLASTICS

[75] Inventors: Dieter Regnat, Frankfurt am Main; Manfred Böhshar, Kelkheim; Hans-Jerg Kleiner, Kronberg/Taunus; Gerhard Pfahler, Augsburg, all of Fed. Rep. of Germany

[73] Assignee: Hoechst Aktiengesellschaft, Frankfurt am Main, Fed. Rep. of Germany

[21] Appl. No.: 920,112

[22] Filed: Jul. 24, 1992

[30] Foreign Application Priority Data

Jul. 26, 1991 [DE] Fed. Rep. of Germany ....... 4124790

[51] Int. Cl.$^5$ .................. C08K 5/5377; C07F 9/46
[52] U.S. Cl. .................. 524/151; 524/129; 524/148; 558/70; 558/134; 558/155; 558/158; 558/190; 558/197
[58] Field of Search ............. 524/129, 148, 151; 558/158, 155, 134, 70, 190, 197

[56] References Cited

U.S. PATENT DOCUMENTS

| | | | |
|---|---|---|---|
| 2,274,291 | 2/1942 | Clayton et al. | 558/70 |
| 3,050,499 | 8/1962 | Gordon et al. | 524/151 |
| 3,316,333 | 4/1967 | Hechenbleikner et al. | 558/70 |
| 3,354,118 | 11/1967 | Mauz et al. | 524/151 |
| 3,403,186 | 9/1968 | Schlicting et al. | 568/702 |
| 3,414,538 | 12/1968 | Prinz et al. | 524/151 |
| 3,422,059 | 1/1969 | Taylor et al. | 524/291 |
| 3,809,676 | 5/1974 | Liberti | 524/133 |
| 3,932,318 | 1/1976 | Vogl | 521/158 |
| 3,953,388 | 4/1976 | Liberti . | |
| 3,954,860 | 5/1976 | Birum | 528/126 |
| 4,025,570 | 5/1977 | Cramer . | |
| 4,219,607 | 8/1980 | Cammack et al. | 174/110 |
| 4,223,071 | 9/1980 | Boyer et al. . | |
| 4,520,151 | 5/1985 | Chasar | 524/150 |

FOREIGN PATENT DOCUMENTS 49-107050 11/1974 Japan .
WO14349 11/1990 World Int. Prop. O. .

OTHER PUBLICATIONS

Chemical Abstracts, vol. 97; No. 144935j; (1982); & ZH.Obshch.Khim.Bd. 52, Nr. 6 (1982), pp. 1270–1277. R. D. Gareev et al.

J. Gloede et al: Z. Anorg. Allg. Chem. 535 (1986) 221–228.

Primary Examiner—Veronica P. Hoke

[57] ABSTRACT

Diarylphosphinous acid aryl esters are made by the disclosed process. These compounds are useful for stabilizing plastics, in particular polymerization plastics, and hence can be incorporated into a plastic molding composition.

8 Claims, No Drawings

DIARYLPHOSPHINOUS ACID ARYL ESTERS, A PROCESS FOR THEIR PREPARATION AND THEIR USE FOR STABILIZING PLASTICS

The present invention relates to novel diarylphosphinous acid aryl esters, a process for their preparation and their use for stabilizing plastics, in particular polyolefins.

It is known that synthetic polymers must be protected from undesirable oxidative, thermal and photochemical damage by using stabilizers or stabilizer systems during their preparation, processing and use. Such stabilizers consist, for example, of a phenolic antioxidant, which is to ensure, in particular, the long-term stability of the finished component during use, and one or more costabilizers, which regulate the processing stability and in some cases also synergistically intensify the action of the phenolic component.

The customary costabilizers include, for example, orthoalkylated arylphosphites and phosphonites.

The phosphonous acid diaryl esters described in U.S. Pat. Nos. 4,406,842 and 4,474,914 often do not have satisfactory stabilizer properties, and furthermore their synthesis is based on organodichlorophosphanes, which are accessible with difficulty on an industrial scale.

In practice, the only precursor which is available on an industrial scale is phenyldichlorophosphane, from which exclusively benzenephosphonous acid diesters are accessible. However, the desired properties of stabilizers are often only achieved by more highly substituted aryl groups on the phosphorus.

It is known from AU-OS 90/56 539 that phosphonites can be prepared by reaction of phosphorous acid diesterchlorides with Grignard reagents. Although the stabilizers thus obtained have more highly substituted aryl groups on the phosphorus, the disadvantage of using phosphites and phosphonites is that acid products may be obtained during their hydrolysis.

The object of the present invention was therefore to provide novel phosphorus stabilizers which on the one hand meet the high requirements in practice, and in particular also do not dissociate into acid secondary products under the action of water, but at the same time can be prepared in a simple manner and in a high yield by ecologically favorable processes.

It has now been found, surprisingly, that diarylphosphinous acid aryl esters of the formula (I) (see patent claim 1) meet these requirements to a high degree.

The invention therefore relates to diarylphosphinous acid aryl esters of the formula (I), i.e. phosphinous acid aryl esters where n=1 and diphosphinous acid diaryl esters where n=2, in which $R^1$ and $R^2$ independently of one another, as monovalent radicals, are a phenyl or naphthyl radical, each of which can carry 1 to 5 substituents, in which the substituents are identical or different and are a nonaromatic hydrocarbon radical, an alkoxy radical, alkylthio radical or dialkylamino radical having in each case 1 to 8 carbon atoms, aryl or aryloxy having in each case 6 to 10 carbon atoms or halogen having an atomic number of 9 to 35, and $R^2$, as a divalent radical, is a phenylene or biphenylene radical, which is unsubstituted or substituted by up to 4 nonaromatic hydrocarbon radicals having 1 to 8 carbon atoms, or a naphthylene radical, which is unsubstituted or carries 1 to 4 nonaromatic hydrocarbon radicals having 1 to 8 carbon atoms as substituents, and $R^3$, $R^4$ and $R^5$ independently of one another are hydrogen or a branched or unbranched hydrocarbon radical having 1 to 8 carbon atoms, preferably having 1 to 4 carbon atoms.

Monovalent radicals which may be mentioned specifically for $R^1$ and $R^2$ are, for example, the various tolyl radicals and xylyl radicals, mesityl, 2,4,5-trimethylphenyl, the various tert-butylphenyl radicals and di-tert-butylphenyl radicals, 2,4,6-tri-tert-butylphenyl, 2,4-di-tert-octylphenyl and the various biphenyl, methylnaphthyl, dimethylnaphthyl and trimethylnaphthyl radicals.

Examples of a divalent radical $R^2$ which may be mentioned are the various phenylene radicals, such as 1,3- and 1,4-phenylene, the various biphenylene radicals, such as 2',3-, 2',4-, 3',3-, 3',4- and 4,4'-biphenylene, and the various naphthylene radicals, such as 1,4- and 1,6-naphthylene.

Suitable radicals $R^3$, $R^4$ and $R^5$ are, f or example, non-aromatic hydrocarbon radicals having 1 to 18 carbon atoms, such as alkyl or cycloalkyl, and furthermore aromatic radicals, which contain 6 to 18 carbon atoms, including aliphatic groups, not more than 10 carbon atoms being part of an aromatic ring system. The radicals $R^3$, $R^4$ and $R^5$ preferably contain 4 to 12 and in particular 6 to 10 carbon atoms. Suitable nonaromatic hydrocarbon radicals are, specifically, alkyl, such as methyl, ethyl and the various propyl, butyl, pentyl, hexyl, octyl, decyl, dodecyl, hexadecyl and octadecyl radicals, and cycloalkyl having 5 to 10 carbon atoms, such as cyclopentyl, cyclohexyl, cycloheptyl and cyclohexylmethyl (i.e. both the hydrogenated benzyl radical and the methylcyclohexyl radical);furthermore, $C_6C_{10}$-aryl and arylmethyl may be mentioned, wherein the term aryl in each case includes alkylaryl, carries not more than three of the substituents mentioned under $R^1$ and, including these, has not more than 14 carbon atoms.

If the radicals $R^3$, $R^4$ and $R^5$ are alkyl radicals, tertiary alkyl radicals having 4–10 carbon atoms, such as tert-butyl, 2-methyl-2-butyl, 2-methyl-2-pentyl and 2-ethyl-2-butyl, are particularly preferred.

Examples of specific compounds of the formula (I) are:
2,4,6-trimethylphenyl-phenylphosphinous acid 2,4-di-tert-butylphenyl ester
2,4,6-trimethylphenyl-l-naphthylphosphinous acid 2,4-di-tert-butylphenyl ester
bis-(4-biphenyl)phosphinous acid 2,4-di-tert-butylphenyl ester
bis-(1-naphthyl)phosphinous acid 2,4-di-tert-butylphenyl ester
4,4'-biphenylene-bis-(1-naphthyl phosphinous acid 2,4-di-tert-butylphenyl ester)
2,4,6-trimethylphenyl-4-methoxyphenylphosphinous acid 2,4,6-tri-tert-butylphenyl ester
bis-(4-chlorophenyl)phosphinous acid 2-tert-butylphenyl ester
bis-(2-methoxyphenyl)phosphinous acid 2,4-di-tert-butylphenyl ester
1,4-phenylene-bis-(l-naphthylphosphinous acid 2,4,6-tri-tert-butylphenyl ester)
1,4-naphthylene-bis(l-naphthylphosphinous acid 2,4-di-tert-butylphenyl ester)
bis-[4- (N,N-dimethylamino)phenyl]phosphinous acid 2,4-di-tert-butylphenyl ester
1-naphthyl-2-methoxyphenylphosphinous acid 2,4-di-tert-butylphenyl ester
1-naphthyl-4-tert-butylphenylphosphinous acid 2,6-di-tert-butylphenyl ester 4,4′-biphenylene-bis-(2,4,6-trimethylphenylphosphinous acid 2,4-di-tert-butylphenyl ester)

The invention also relates to a process for the preparation of the phosphinous acid esters of the formula (I) in which $R^1$ and $R^2$ have the abovementioned meaning, which comprises a) first reacting, in a first stage, a hydrocarbon halide $R^1$-Hal in which $R^1$ has the abovementioned meaning and the halogen of which has an atomic weight of at least 35, but is chlorine or bromine and particularly preferably bromine, under Grignard conditions, advantageously with intimate mixing, with at least the stoichiometric amount of finely divided magnesium to give the corresponding Grignard compound $R^1$-MgHal, reacting this further, in a second stage, with a phosphorous acid aryl ester-dichloride, reacting, in a third stage, a halide $R^2$-$(Hal)_n$, in which $R^2$ and the halogen have the abovementioned meaning and n is 1 or 2, under Grignard conditions, advantageously with intimate mixing, with at least the stoichiometric amount of finely divided magnesium to give the corresponding Grignard compound $R^2$-$(MgHal)_n$, and reacting this, in a fourth stage, with the phosphonous acid ester-halide of the formula (II) (see patent claim 1) obtained in the second stage, or b) if $R^1 = R^2$ and n is 1, first reacting, in a first stage, a halide $R^1$-Hal, in which $R^1$ and the halogen have the abovementioned meaning, under Grignard conditions, advantageously with intimate mixing, with at least the stoichiometric amount of finely divided magnesium to give the corresponding Grignard compound $R^1$—Mg-Hal, and, in a second stage, reacting two parts of the Grignard compound with one part of a phosphorous acid aryl ester-dichloride.

Of the phosphorous acid aryl ester-dichlorides employed as starting compounds, phosphorous acid 2,4-di-tert-butylphenylester-dichloride is particularly preferred.

The hydrocarbon halide $R^1$-Hal which is preferably employed for the first stage of process variant a) is preferably one in which $R^1$ is a phenyl radical substituted by at least one of the substituents mentioned, the substituent preferably being in the 2-position, or is an optionally substituted naphthyl radical.

The respective first and where appropriate third stage of the process according to the invention, which can be carried out per se in any customary manner, are preferably carried out in an aprotic, organic solvent, such as an ether, for example diethyl, dipropyl or diisopropyl ether, ethylene glycol dimethyl or -ethyl ether, diethylene glycol dimethyl or -ethyl ether, methyl tert-butyl ether, dioxane or tetrahydrofuran.

Since the Grignard compounds are sensitive to hydrolysis and oxidation, it may be appropriate to carry out the reactions under an inert gas atmosphere. However, such a procedure is in no way essential for the success of the reaction. Suitable inert gases are nitrogen and argon. The reaction temperature is in general between 20° and 125° C., but preferably between 30° and 70° C. It may be advantageous to ensure good fluidization during the Grignard reaction, for example by the action of ultrasound.

To prepare the intermediate products of the formula (II), in the second stage of process variant a) the solution or suspension of the Grignard reagent is metered into a solution of phosphorous acid 2,4-di-tert-butylphenyl ester-dichloride, advantageously at a temperature of below 0° C., with vigorous mixing.

To prepare the compounds (I) where $R^1 = R^2$ (second stage of variant b) and for the reaction of the intermediate products (II) with Grignard compounds (fourth stage of variant a), the reaction partners can be brought together in any desired manner. Preferably, the solution or suspension of the Grignard compound is metered into a solution of the phosphorous acid 2,4-di-tert-butylphenyl ester-dichloride, advantageously at a temperature of below 0° C., with vigorous mixing.

Possible diluents for the second and fourth stage of variant a and f or the second stage of variant b are inert, aprotic solvents, for example an aliphatic hydrocarbon fraction, hexane, cyclohexane, methylcyclohexane, toluene or xylenes, or one of the abovementioned ethers or corresponding mixtures. The reaction temperature in these stages is in general between −30° and +50° C., but preferably between −20° and +20° C. The reaction as a rule proceeds exothermically; accordingly, it may be appropriate to control the course of the reaction by cooling. The most favorable results are achieved if the reaction partners are employed in the stoichiometric amounts. However, it is also possible to employ one reaction partner in excess; in general, however, no particular advantages are associated with this procedure. The mixture is advantageously stirred until the reaction is complete, and the magnesium halide which has precipitated is then separated off. The solvents can be removed from the filtrate in a customary manner, advantageously by distillation, in particular under reduced pressure.

The products (I) can be separated from the crude products by any desired processes, but preferably by crystallization.

In the synthesis of phosphinous acid esters by reaction of phosphorous acid ester-dihalides with organomagnesium halides, replacement of the OR radical by the Grignard compound proceeds as a yield-reducing side reaction, so that even in the most favorable cases, the yields achieved do not exceed 60% [Houben-Weyl: "Methoden der organischen Chemie (Methods of organic chemistry)", 12/1, page 210 (196.3)]. Moreover, there was a prejudice in the literature to the effect that the reaction of phosphorous acid ester-dihalides with organomagnesium bromides initially always leads to insoluble complex compounds which first have to be dissociated by addition of further auxiliaries (for example 4 mol of pyridine) to allow isolation of the desired phosphinous acid esters (Houben-Weyl, loc. cit.). It is therefore particularly surprising that the process of the present invention, specifically in the case where $R^3$ and $R^4$ are tert-butyl and $R^5$ is hydrogen, renders the phosphinous acid esters (I) accessible in a high yield and purity without the use of decomplexing agents being necessary.

The preparation of the phosphorous acid aryl ester-dichlorides required as the precursor is described, for example, in Houben-Weyl: "Methoden der organischen Chemie (Methods of organic chemistry)", volume E1, pages 353-354 (1982).

Finally, the invention relates to the use of compounds of the formula (I), by themselves or in combination with a phenolic antioxidant, for stabilizing plastics, preferably polymerization plastics such as polypropylene. The purity of the crude reaction products obtained is often adequate for this use. Isolation in a pure form is then not necessary.

The present invention thus also relates to a plastics molding composition comprising a thermoplastic or a thermosetting plastic and a diarylphosphinous acid aryl ester of the formula (I) in a ratio of (90 to 99.99):(0.01 to 10). In general only one compound of the compounds of the formula (I) is employed here, but mixtures are also possible.

The plastics molding composition according to the invention comprises a thermoplastic or thermosetting organic polymer, for example one of those listed below:

1. Polymers of mono- and diolefins, for example polyethylene of high, medium or low density (which may optionally be crosslinked), polypropylene, polyisobutylene, polybut-1-ene, polymethylpent-1-ene, polyisoprene or polybutadiene, and polymers of cycloolefins, such as cyclopentene or norbornene.

2. Mixtures of the polymers mentioned under 1), for example of polypropylene with polyethylene or with polyisobutylene.

3. Copolymers of mono- and diolefins with one another or with other vinyl monomers, such as ethylene/propylene copolymers, propylene/but-1-ene copolymers, propylene/isobutylene copolymers, ethylene/but-1-ene copolymers, propylene/butadiene copolymers, iso-butylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), as well as terpolymers of ethylene with propylene and a diene, such as hexadiene, cyclopentadiene or ethylidenenorbornene.

4. Polystyrene.

5. Copolymers of styrene or a-methylstyrene with dienes or acrylic derivatives, such as styrene/butadiene, styrene/maleic anhydride, styrene/acrylonitrile, styrene/ethyl methacrylate, styrene/butadiene/ethyl acrylate and styrene/acrylonitrile/methyl acrylate; high impact strength mixtures of styrene copolymers and another polymer, such as a polyacrylate, a diene polymer or an ethylene/propylene/diene terpolymer; and block copolymers of styrene, such as styrene/butadiene/styrene, styrene/isoprene/styrene, styrene/ethylene-butylene/styrene or styrene/ethylene-propylene/styrene.

6. Graft copolymers of styrene, such as styrene on polybutadiene, styrene and acrylonitrile on polybutadiene (ABS), styrene and maleic anhydride on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5), which are known, for example, as so-called ABS, MBS, ASA or AES polymers.

7. Halogen-containing polymers, such as polychloroprene, chlorinated rubber, chlorinated (CPE) or chlorosulfonated polyethylene, epichlorohydrin homo- and copolymers and in particular polymers of halogen-containing vinyl compounds, such as polyvinyl chloride (PVC), polyvinylidene chloride (PVDC), polyvinyl fluoride and polyvinylidene fluoride (PVDF); and copolymers thereof, such as vinyl chloride/vinylidene chloride, vinyl chloride/vinyl acetate or vinylidene chloride/vinyl acetate.

8. Polymers which are derived from $\alpha,\beta$-unsaturated carboxylic acids and derivatives thereof, such as polyacrylates and polymethacrylates, polyacrylamides and polyacrylonitriles.

9. Copolymers of the monomers mentioned under 8) with one another or with other unsaturated monomers, such as acrylonitrile/butadiene copolymers, acrylonitrile/alkyl acrylate copolymers, acrylonitrile/alkoxy acrylate copolymers, acrylonitrile/vinyl halide copolymers or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, stearate, benzoate or maleate, polyvinyl butyral, polyallyl naphthalate and polyallylmelamine.

11. Homo- and copolymers of cyclic ethers, such as polyethylene glycols, polyethylene oxide, polypropylene oxide or copolymers thereof with bisglycidyl ethers.

12. Polyacetals, such as polyoxymethylene (POM), and those polyoxymethylenes which comprise comonomers such as ethylenoxy.

13. Polyphenylene oxides and sulfides.

14. Polyurethanes (PUR) which are derived from polyethers, polyesters and polybutadienes having terminal hydroxyl groups on the one hand and aliphatic or aromatic polyisocyanates on the other hand, and precursors thereof (polyisocyanate/polyol prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethyleneterephthalamide, poly-m-phenyleneisonaphthalamide and copolymers thereof with polyethers, such as with polyethylene glycol, polypropylene glycol or polytetramethylene glycol.

16. Polyureas, polyimides and polyamide-amides.

17. Polyesters which are derived from dicarboxylic acids and diols and/or from hydroxycarboxylic acids or the corresponding lactones, such as polyethylene terephthalate, polybutylene terephthalate (PBTP), poly-1,4-dimethylolcyclohexane terephthalate, poly-(2,2-bis(4-hydroxyphenyl)-propane) terephthalate and polyhydroxybenzoates, as well as block polyetheresters which are derived from polyethylene having hydroxyl end groups, dialcohols and dicarboxylic acids.

18. Polycarbonates (PC).

19. Polysulfones and polyether-sulfones.

20. Crosslinked polymers which are derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins which are derived from copolyesters of saturated and unsaturated dicarboxylic acids with polyhydric alcohols and also vinyl compounds as crosslinking agents, as well as halogen-containing, poorly combustible modifications thereof.

23. Crosslinkable acrylic resins which are derived from substituted acrylic acid esters, such as from epoxyacrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Naturally occurring polymers, such as cellulose, natural rubber, gelatine and polymer-homologously chemically modified derivatives thereof, such as cellulose acetates, propionates and butyrates, and the cellulose ethers, such as methyl cellulose.

27. Mixtures of the abovementioned polymers, such as, for example, PP/EPDM, polyamide 6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, polyphenylene ether/high impact strength polystyrene (PPE/HIPS), PPE/polyamide 6.6 and copolymers, PA/HDPE, PA/PP and PA/PPE.

28. Naturally occurring and synthetic organic substances which are pure monomers or mixtures of monomers, such as mineral oils, animal and vegetable fats, oils and waxes or oils, fats and waxes based on synthetic esters, or mixtures of these substances.

29. Aqueous dispersions of natural and synthetic rubber.

The polymer is preferably a polyolefin, in particular polypropylene. The proportion of polymers in the molding composition according to the invention is 90 to 99.99, preferably 98 to 99.98 % by weight.

The molding composition comprises, as a stabilizer, a diarylphosphinous acid aryl ester of the formula (I) and if appropriate a phenolic antioxidant.

The phenolic antioxidant is, for example, an ester of 3,3-bis-(3'-butyl-4'-hydroxyphenyl)-butanoic acid of the formula (III)

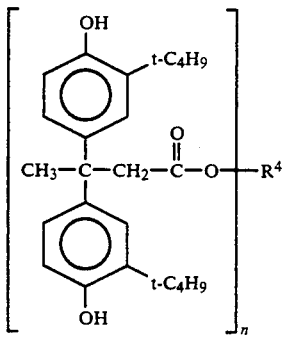

(III)

in which n is 1 or 2 and $R^4$ is a $C_1$–$C_{18}$-alkyl radical, if n is 1, or is a $C_1$–$C_{12}$-alkylene radical, if n is 2. Preferably, $R_4$ is a $C_2$–$C_4$-alkylene radical, in particular a $C_2$-alkylene radical.

However, the phenolic antioxidant can also be an ester of β-(3,5-di-t-butyl-4-hydroxy-phenyl)-propionic acid of the formula (IV)

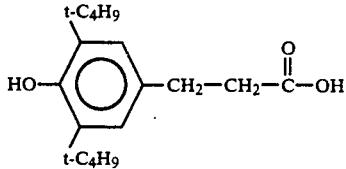

in which the alcohol component is a mono- to tetrahydric alcohol, such as methanol, octadecanol, 1, 6-hexanediol, neopentylglycol, diethylene glycol, triethylene glycol, pentaerythritol, tris-hydroxyethyl isocyanurate, thiodiethylene glycol or dihydroxyethyl-oxalic acid diamide.

The novel stabilizers are incorporated into the organic polymers by generally customary methods. The incorporation can be carried out, for example, by addition of the stabilizers before or during the polymerization, polycondensation or polyaddition, or by mixing the compounds and if appropriate other additives into the melt before or during shaping. The incorporation can also be carried out by application of the dissolved or dispersed compounds to the polymer directly or by mixing them into a solution, suspension or emulsion of the polymer, the solvent subsequently being allowed to evaporate if appropriate. The amount to be added to the polymer is 0.01 to 10, preferably 0.025 to 5, in particular 0. 05 to 1.0% by weight, based on the material to be stabilized.

The novel compounds can also be added in the form of a masterbatch, which contains these compounds, for example, in a concentration of 1 to 50, preferably 2.5 to 20% by weight, to the polymers to be stabilized.

The molding composition according to the invention can also additionally contain other antioxidants, such as 1. alkylated monophenols, for example 2,6-di-t-butyl-4-methylphenol, -4-ethylphenol, -4-n-butylphenol and -4-i-butylphenol, 2-t-butyl-4,6-dimethylphenol, 2,6-dicyclopentyl-4-methylphenol, 2-(α-methylcyclohexyl)-4,6-dimethylphenol, 2,6-dioctadecyl-4-methylphenol, 2,4,6-tri-cyclohexylphenol and 2,6-di-t-butyl-4-methoxymethylphenol;

2. alkylated hydroquinones, such as 2,5-di-t-butyl- and 2,5-di-t-amyl-hydroquinone, 2,6-di-t-butyl-4-methoxyphenol and 2,6-diphenyl-4-octadecylphenol;

3. hydroxylated thiodiphenyl ethers, such as 2, 2'-thiobis- (6-t-butyl-4-methylphenol) and -(4-octylphenol), as well as 4,4'-thio-bis-(6-t-butyl-3-methylphenol) and -(6-t-butyl-2-methylphenol);

4. alkylidene-bisphenols, such as 2,2'-methylene-bis-(6-t-butyl-4-methylphenol), -(6-t-butyl-4-ethylphenol), -[4-methyl-6- (=-methylcyclohexyl)-phenol], -(4-methyl-6-cyclohexylphenol) , -(6-nonyl-4-methylphenol), -(4,6-di-t-butylphenol), -[6-(α-methylbenzyl)-4-nonylphenol], -[6-(α,α-dimethylbenzyl)-4-nonylphenol], 4,4'-methylene-bis-(2,6-di-t-butylphenol), -(6-t-butylphenol) and -(6-t-butyl-4-isobutylphenol), 1, 1-bis- and 1, 1, 3-tris- (5-t-butyl-4-hydroxy-2-methylphenyl)-butane, 2,6-di-(3-t-butyl-5-methyl-2-hydroxybenzyl)-4-methylphenol, 1,1-bis(5-t-butyl-4-hydroxy-2-methylphenyl)-3-n-dodecylmercaptobutane and di- (3-t-butyl-4-hydroxy-5-methylphenyl)-dicyclopentadiene;

5. benzyl compounds, such as di-[2-(3'-t-butyl-2'-hydroxy-5'-methyl-benzyl) -6-t-butyl-4-methyl-phenyl] terephthalate, 1,3,5-tri-(3,5-di-t-butyl-4-hydroxybenzyl)-2,4,6-trimethylbenzene, di-(3,5-di-t-butyl-4-hydroxybenzyl) sulfide, isooctyl 315-di-t-butyl-4-hydroxybenzyl-mercaptoacetate, bis-(4-t-butyl-3-hydroxy-2,6-dimethylbenzyl) dithiol-terephthalate, 1,3,5-tris-(3,5-di-t-butyl-4-hydroxybenzyl) iso-cyanurate, 1,3,5-tris-(4-t-butyl-3-hydroxy-2,6-dimethylbenzyl) isocyanurate, dioctadecyl 3,5-di-t-,-butyl-4-hydroxybenzyl phosphonate and the calcium salt of monoethyl 3,5-di-t-butyl-4-hydroxybenzylphosphonate;

6. acylaminophenols, such as 4-hydroxy-lauric and -stearic acid anilide, 2,4-bis-octylmercapto-6-(3,5-di-t-butyl-4-hydroxy-anilino)-s-triazine and octyl N-(3,5-di-t-butyl-4-hydroxyphenyl) carbamate;

7. esters of β-(5-t-butyl-4-hydroxy-3-methylphenyl)-propionic acid with mono- or polyhydric alcohols, such as methanol, octadecanol, 1,6-hexanediol, neopentylglycol, diethylene glycol, triethylene glycol, pentaerythritol, tris-hydroxyethyl isocyanurate, thiodiethylene glycol or dihydroxyethyl-oxalic acid diamide; and 8. amides of β-(3,5-di-t-butyl-4-hydroxyphenyl)-propionic acid, such as N,N'-di-(3,5-di-t-butyl-4-hydroxyphenylpropionyl)-trimethylenediamine, -hexamethylenediamine and -hydrazine.

In addition, the molding composition according to the invention can also contain other additives, such as
1. UV absorbers and light stabilizers, for example
1.1 2-(2'-hydroxymethyl)-benzotriazoles, such as the 5'-methyl, 3',5'-di-t-butyl, 5'-t-butyl, 5'-(1,1,3,3-tetramethylbutyl)-, 5-chloro-3',5'-di-t-butyl-, 5-chloro-3'-t-butyl-5'-methyl-, 3'-sec-butyl-5'-t-butyl-, 4'-octoxy-, 3',5'-di-t-amyl and 3',5'-bis-(α,α-dimethyl-benzyl) derivatives;
1.2 2-hydroxybenzophenones, such as the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives;
1.3 esters of optionally substituted benzoic acids, such as phenyl salicylate, 4-t-butyl-phenyl salicylate, octylphenyl salicylate, dibenzoylresorcinol, bis-(4-t-butyl-benzoyl)-resorcinol, benzylresorcinol, 2,4-di-t-butylphenyl 3,5-di-t-butyl-4-hydroxy-benzoate and hexadecyl 3,5-di-t-butyl-4-hydroxybenzoate;
1.4 acrylates, such as ethyl or iso-octyl α-cyano-β,β-diphenylacrylate, methyl α-carbomethoxy- and α-carbomethoxy-p-methoxy-cinnamate, methyl or butyl α-cyano-β-methyl-p-methoxy-cinnamate and N-(β-carbomethoxy-β-cyano-vinyl)-2-methyl-indoline;
1.5 nickel compounds, such as nickel complexes of 2,2'-thio-bis-[4-(1,1,3,3-tetramethyl-butyl)-phenol], such as the 1:1 or 1:2 complex, if appropriate with additional ligands, such as n-butylamine, triethanolamine or N-cyclohexyldiethanolamine, nickel alkyl-dithiocarbamates, nickel salts of monoalkyl 4-hydroxy-3,5-di-t-butyl-benzylphosphonates, such as of the methyl or ethyl ester, nickel complexes of ketoximes, such as of 2-hydroxy-4-methylphenyl undecyl ketone oxime, nickel salts of 2-hydroxy-4-alkoxybenzophenones and nickel complexes of 1-phenyl-4-lauroyl-5-hydroxy-pyrazole, if appropriate with additional ligands;
1.6 sterically hindered amines, such as
1.6.1. bis-(2,2,6,6-tetramethylpiperidyl) sebacate, glutarate and succinate, 4-stearyloxy- and 4-stearoyloxy-2,2,6,6-tetramethyl-piperidine, 4-stearyloxy- and 4-stearoyloxy-1,2,2,6,6-pentamethyl-piperidine, 2,2,6,6-tetramethylpiperidyl behenate, 1,2,2,6,6-pentamethylpiperidinyl behenate, 2,2,4,4-tetramethyl-7-oxa-3,20-diazadispiro-[5.1.11.2)-heneicosan-21-one, 2,2,3,4,4-pentamethyl-7-oxa-3,20-diaza-dispiro-[5.1.11.2]-heneicosan-21-one, 2,2,4,4-tetramethyl-3-acetyl-7-oxa-3,20-diaza-dispiro[5.1.11.2]-heneicosan-21-one, 2,2,4,4-tetra-methyl-7-oxa-3,20-diaza-20-(β-lauryl-oxycarbonylethyl)-21-oxo-dispiro-[5.1.11.2]-heneicosane, 2,2,3,4,4-pentamethyl-7-oxa-3,20-diaza-20-(β-lauryloxycarbonylethyl)-21-oxo-dispiro-[5.1.11.2]-heneieicosane, 2,2,4,4-tetramethyl-3-acetyl-7-oxa-3,20-diaza-20-(β-lauryloxycarbonyl ethyl)-21-oxo-dispiro-[5.1.11.2]-heneicosane, 1,1',3,3',5,5'-hexahydro-2,2',4',4,6,6'-hexaaza-2,2',6,6'-bismethano-7,8-dioxo-4,4'-bis-(1,2,2,6,6-penetamethyl-4-piperidyl)-biphenyl, N,N',N'',N'''-tetrakis-{2,4-bis-[N-(2,2,6,6-tetramethyl-4-piperidyl)-butyl-amino]-1,3,5-triazin-6-yl }-4,7-diazadecane-1,10-diamine, N,N'',N',N'',-tetrakis-{2,4-bis-[N-(1,2,2,6,6-pentamethyl-4-piperidyl)-butylamino]-1,3,5-triazin-6-yl }-4,7-diazadecane-10-diamine, N,N',N''',N''''-tetrakis-{2,4-bis-[N-(2,2,6,6-tetramethyl-4-piperidyl)-methoxypropylamino]-1,3,5-triazin-6-yl}-4,7-diazadecane-1,10-diamine, N,N', N'', N''''-tetrakis-{2,4-bis[N-(1,2,2,6,6-pentamethyl-4-piperidyl)-methoxypropylamino]-1,3,5-triazin-6-yl}-4,7-diazadecane-1,10-diamine, bis-(1,2,2,6,6-pentamethyl-piperidyl) n-butyl-3,5-di-tert-butyl-4-hydroxy-benzylmalonate, tris-(2,2,6,6-tetramethyl-4-piperidyl) nitrilotriacetate, tetrakis-(2,2,6,6-tetramethyl-4-piperidyl) -1,2,3,4-butanetetracarboxylic acid and 1,1'-(1,2-ethanediyl)-bis-(3,3,5,5-tetramethylpiperazinone).
1.6.2. Poly-N,N'-bis-(2,2,6,6-tetramethyl-4-piperidyl)-1,8-diazadecylene, the condensation product of 1-(2-hydroxyethyl)-2,2,6,6-tetramethyl-4-hydroxypiperidine and succinic acid, the condensation product of N,N'-bis-(2,2,6,6-tetramethyl-4-piperidyl)-hexamethylenediamine and 4-tert-octylamino-2,6-dichloro-1,3,5-s-triazine, and the condensation product of N,N'-bis-(2,2,6,6-tetramethyl-4-piperidyl)-hexamethylenediamine and 4-morpholino-2,6-dichloro-1,3,5-triazine.
1.6.3. N-Oxyalkyl derivatives of the 2,2,6,6-tetramethylpiperidine derivatives mentioned under 1.6.1. and 1.6.2., in which the alkyl is $C_1$–$C_{18}$-alkyl.

A combination of the compounds according to the invention proves to be particularly advantageous here in many cases.

1.7 Oxalic acid diamides, such as 4,4'-dioctyloxyoxanilide, 2,2'-di-octyloxy-5,5'-di-t-butyloxanilide, 2,2'-didodecyloxy-5,5'-di-t-butoxyanilide, 2-ethoxy-2'-ethyloxanilide, N,N'-bis-(3-dimethylaminopropyl)-oxalamide, 2-ethoxy-5-t-butyl-2'-ethyloxanilide and a mixture thereof with 2-ethoxy-2'-ethyl-5,4-di-t-butyloxanilide, and mixtures of o- and p-methoxy- and -ethoxy-di-substituted oxanilides;

2. metal deactivators, such as N,N'-diphenyloxalic acid diamide, N-salicylal-N'-salicyloyl-hydrazine, N,N'-bis-salicyloyl-hydrazine, N,N'-bis-(3,5-di-t-butyl-4-hydroxyphenylpropionyl)-hydrazine, 3-salicyloylamino-1,2, 3-triazole and bis-benzylidene-oxalic acid dihydrazide;

3. phosphites and phosphonites, for example triphenyl phosphite, diphenyl alkyl phosphites, phenyl dialkyl phosphites, trisnonylphenyl phosphite, trilauryl phosphite, trioctadecyl phosphite, distearyl pentaerythrityl diphosphite, tris(2,4-di-t-butylphenyl) phosphite, diisodecyl pentaerythrityl diphosphite, bis-(2,4-di-t-butylphenyl) pentaerythrityl diphosphite, tristearyl sorbityl triphosphite, tetrakis-(2,4-di-t-butylphenyl) 4,4'-biphenylenediphosphonite, 3,9-bis-(2,4-di-t-butyl-phenoxy)-2,4,8,10-tetraoxa-3,9-diphosphaspiro[5.5]undecane and tris(2-t-butyl-4-thio(2'-methenyl-4'-hydroxy-5'-t-butyl)-phenyl-5-methenyl)-phenylphosphite;

4. compounds which destroy peroxide, such as esters of β-thio-dipropionic acid, for example the lauryl, stearyl, myristyl or tridecylester, mercaptobenzimidazole, the zink salt of 2-mercaptobenzimidazole, zink alkyl-dithiocarbamates, dioctadecyldisulfide, dioctadecylmonosulfide and pentaerythritol tetrakis-(β-dodecyl-mercapto)-propionate;

5. basic costabilisers, such as melamine, polyvinylpyrrolidone, dicyandiamide, triallyl cyanurate, urea derivatives, hydrazine derivatives, amines, polyamines, polyurethanes, alkali metal and alkaline earth metal salts of higher fatty acids or phenolates, for example Ca stearate, Zn stearate and Mg stearate, Na ricinoleate, K palmitate, antimony pyrocatecholate or tin pyrocatecholate, and hydroxides and oxides of alkaline earth metals or of aluminum, for example CaO, MgO or ZnO;

6. nucleating agents, such as 4-t-butylbenzoic acid, adipic acid, diphenylacetic acid and dibenzylidenesorbitol;
7. fillers and reinforcing agents, such as calcium carbonate, silicates, glass fibers, asbestos, talc, kaolin, mica, barium sulfate, metal oxides and hydroxides, carbon black and graphite; and
8. other additives, such as plasticizers, lubricants, emulsifiers, pigments, optical brighteners, flame-proofing agents, antistatics and blowing agents.

The various additional additives of the abovementioned groups 1 to 6 are added to the polymers to be stabilized in an amount of 0.01 to 10, preferably 0.02 to 5% by weight, based on the total weight of the molding composition. The amount of additives of groups 7 and 8 is in general 1 to 80, preferably 10 to 50% by weight, based on the total molding composition.

The organic polymers stabilized according to the invention can be used in various forms, for example as films, fibers, tapes or profiles, or as binders for paints, adhesives or putties.

1. Examples for the preparation of the diarylphosphinous acid aryl esters

General instructions for compounds of the formula (I)

Process variant a

The corresponding Grignard compound $R^1$-MgBr was prepared 15 from 150 mmol of organobromine compound $R^1$-Br and 150 mmol (=3.65 g) of magnesium filings in 90 ml of tetrahydrofuran under a nitrogen atmosphere and with exclusion of moisture. The resulting solution or suspension of the organometallic compound was then metered into a solution of 150 mmol (=46.1 g) of phosphorous acid 2,4-di-tert-butylphenyl ester-dichloride in 120 ml of tetrahydrofuran/n-heptane (1:1) in the course of 30 to 40 minutes at an internal temperature of $-20°$ to $-10°$ C., while stirring vigorously. The reaction mixture was subsequently allowed to warm to room temperature and was stirred for a further 2.5 hours in order to bring the reaction to completion. The corresponding Grignard compound $R^2$-(MgBr)$_n$ was prepared from 150 mmol of organo-bromine compound $R^2$-(Br)$_n$ and 150 mmol (=3.65 g) of magnesium filings in 90 ml of tetrahydrofuran under a nitrogen atmosphere and with exclusion of moisture. The resulting solution or suspension of the organometallic compound $R^2$-(MgBr)$_n$ was then metered into a solution of the previously prepared arylphosphonous acid 2,4-di-tert-butylphenyl ester-chloride in the course of 30 to 40 minutes at an internal temperature of $-20°$ to $-10°$ C., while stirring vigorously. The reaction mixture was subsequently allowed to warm to room temperature and was stirred for a further 2.5 hours in order to bring the reaction to completion. After the magnesium salt which had precipitated had been filtered off and washed with about 50 ml of petroleum ether, the solvent was distilled off, first under the vacuum of a water pump and then under a high vacuum. The colorless or beige residue which remained was powdered, and dried under a high vacuum.

Process variant b

The corresponding Grignard compound was prepared from 300 mmol of organobromine compound and 300 mmol (=7.3 g) of magnesium filings in 180 ml of tetrahydrofuran under a nitrogen atmosphere and with exclusion of moisture. The resulting solution or suspension of the organometallic compound was then metered into a solution of 150 mmol (=46.1 g) of phosphorous acid 2,4-di-tert-butylphenyl ester-dichloride in 120 ml of tetrahydrofuran/n-heptane (1:1) in the course of 30 to 40 minutes at an internal temperature of $-20°$ to $-10°$ C., while stirring vigorously. The reaction mixture was subsequently allowed to warm to room temperature and was stirred for a further 2.5 hours in order to bring the reaction to completion. After the magnesium salt which had precipitated had been filtered off and washed with about 50 ml of petroleum ether, the solvent was distilled off, first under the vacuum of a water pump and then under a high vacuum. The colorless or beige residue which remained was powdered, and dried under a high vacuum.

The product content of the crude materials was determined in each case by $^{31}$P-NMR spectroscopy and in general was between 70 and 95% (of the total P). In the cases described, the product was crystallized from suitable solvents for characterization.

1. 2,4,6-Trimethylphenyl-phenylphosphinous acid 2,4-di-tert-butylphenyl ester (variant a): starting from 29.9 g of 1-bromo-2,4,6-trimethylbenzene and 23.6 g of bromobenzene, 64 g of colorless crystals having a melting point of 126° C. and a content of 95% of the above compound [$^{31}$P-NMR: $\delta$(CDCl$_3$)=111.1 PPM] were obtained. Colorless crystals of melting point 128°-130° C. crystallized from acetone.

$C_{29}H_{37}OP$ calculated: 80.52% C, 8.62% H, 7.16% P (432.59) found: 80.3% C, 8.8% H, 7.3% P.

2. 2,4,6-Trimethylphenyl-1-naphthylphosphinous acid 2,4-di-tert-butylphenyl ester (variant a): starting from 29.9 g of 1-bromo-2,4,6-trimethylbenzene and 31.05 g of 1-bromonaphthalene, 71 g of beige crystals having a melting point of 116° C. and a content of 70% of the above compound ("P-NMR: $\delta$(CDCl$_3$)=108.06 ppm] were obtained. Colorless crystals of melting point 118° C. crystallized from acetone/acetonitrile=¼.

$C_{33}H_{39}OP$ calculated: 82.12% C, 8.14% H, 6.42% P (482.62) found: 82.3% C, 8.2% H, 6.3% P.

3. Bis-(4-biphenyl)phosphinous acid 2,4-di-tert-butylphenyl ester (variant b) : starting from 69.3 g of 4-bromobiphenyl, 78 g of colorless crystals having a melting point of 165° C. and a content of 92% of the above compound [$^{31}$P-NMR: $\delta$(CDCl$_3$)=107.48 ppm] were obtained. Colorless crystals of melting point 168°-170° C. crystallized from 2-butanone.

$C_{38}H_{39}OP$ calculated: 84.10% C, 7.24% H, 5.71% P (542.70) found: 84.2% C, 7.3% H, 5.6% P.

4. Bis-(1-naphthyl)phosphinous acid 2,4-di-tert-butylphenyl ester (variant b): starting from 62.1 g of 1-bromonaphthalene, 72 g of colorless crystals having a melting point of 170° to 174° C. were obtained. Colorless crystals of melting point 178° to 180° C. crystallized from acetonitrile. $C_{33}H_{39}op$ calculated: 83.24% C, 7.19% H, 6.31% P (490.62) found: 83.1% C, 7.2% H, 6.3% P.

5. Bis-(1-naphthyl)phosphinous acid 2f4-di-tert-butylphenyl ester (variant b): the procedure was as in Example 4, but, conversely, the solution of phosphorous acid 2,4-di-tert-butylphenyl esterdichloride was metered into the suspension of the Grignard compound. Starting from 62.1 g of 1-bromonaphthalene, 78 g of colorless crystals having a melting point of 174° to 176° C. and a content of 89 % of the above compound [−P-NMR: 67 (CDCl$_3$)=96.16 ppm] were obtained.

6. 4,4'-Biphenylene-bis- (1-naphthyl-phosphinous acid 2,4-di-tert-butylphenyl ester): in deviation from the general instructions, 200 mmol (=62.4 g) of 4,4'-dibromobiphenyl were subjected to a Grignard reaction with 600 mmol (=14.6 g) of magnesium filings in 600 ml of tetrahydrofuran under the action of ultrasound (40 kHz), and the product was then reacted with 400 mmol (=122.9 g) of phosphorous acid 2,4-di-tert-butylphenyl ester-dichloride in 700 ml of tetrahydrofuran/heptane=1/6. The Grignard reagent obtained from 82.8 g (400 mmol) of 1-bromonaphthalene was added dropwise to the resulting suspension. The mixture was filtered and the filtrate was concentrated in vacuo to give 175 g of yellow resin having a content of 76% of the above compound $^{31}$P-NMR: δ(CDCl$_{103.7}$ ppm]. Pale yellow crystals of melting point 255° C. crystallized from acetone.

C$_{60}$H$_{64}$O$_2$P$_{b2}$ calculated: 81.98% C, 7.34% H, 7.05% P (879.12) found: 81.7% C, 7.5% H, 7.2% P.

General instructions for the preparation of the diarylphosphinous acid 2,4-di-tert-butyl esters Method A The corresponding Grignard compound was prepared from 300 mmol of organobromine compound and 300 mmol (=7.3 g) of magnesium filings in 180 ml of tetrahydrofuran under a nitrogen atmosphere and with exclusion of moisture. The resulting solution or suspension of the organometallic compound was then metered into a solution of 150 mmol (=46.1 g) of phosphorous acid 2,4-di-tert-butylphenyl ester-dichloride in 120 ml of tetrahydrofuran/n-heptane (1:1) in the course of 30-40 minutes at an internal temperature of −20° to −10° C., while stirring vigorously. The mixture was then allowed to assume room temperature and was subsequently stirred for a further 2.5 hours in order to bring the reaction to completion. After the magnesium salt which had precipitated had been filtered off and washed with about 50 ml of petroleum ether, the solvents were removed, first under the vacuum of a water pump and then under a high vacuum. The colorless or beige residue which remained was powdered, and dried under a high vacuum.

Method B

The corresponding Grignard compound R$^1$-MgBr was prepared from 150 mmol of organobromine compound R$^1$-Br and 150 mmol (=3.65 g) of magnesium filings in 90 ml of tetrahydrofuran under a nitrogen atmosphere and with exclusion of moisture. The resulting solution or suspension of the organometallic compound was then metered into a solution of 150 mmol (=46.1 g) of phosphorous acid 2,4-di-tert-butylphenyl ester-dichloride in 120 ml of tetrahydrofuran/n-heptane (1:1) in the course of 30-40 minutes at an internal temperature of −20° to −10° C., while stirring vigorously. The mixture was then allowed to assume room temperature and was subsequently stirred for a further 2.5 hours in order to bring the reaction to completion. The corresponding Grignard compound R$^2$-MgBr was prepared from 150 mmol of organobromine compound R$^2$-Br and 150 mmol (=3.65 g) of magnesium filings in 90 ml of tetrahydrofuran under a nitrogen atmosphere and with exclusion of moisture. The resulting solution or suspension of the organometallic compound R$^2$-MgBr was then metered into a solution of the previously prepared arylphosphorous acid 2,4-di-tert-butylphenyl ester-chloride in the course of 30-40 minutes at an internal temperature of −20° to −10° C., while stirring vigorously. The mixture was then allowed to assume room temperature and was subsequently stirred for a further 2.5 hours in order to bring the reaction to completion. After the magnesium salt which had precipitated had been filtered off and washed with about 50 ml of petroleum ether, the solvents were removed, first under the vacuum of a water pump and then under a high vacuum. The colorless or beige residue which remained was powdered, and dried under a high vacuum.

In the cases described, the product content of the crude materials was determined by $^{31}$P-NMR spectroscopy and in general was between 70 and 95% (of the total P). In the cases described, the product was crystallized from suitable solvents for characterization.

7. Bis-4-chlorophenylphosphinous acid 2,4-di-tert-butyl ester: inverse addition: a Grignard reagent was prepared from 57.4 g of 4-chlorobromobenzene. This reagent was cooled to −20° C., and a solution of 150 mmol (=46.1 g) of phosphorous acid 2,4-di-tert-butylphenyl ester-dichloride in 120 ml of tetrahydrofuran/n-heptane (1:1) was metered in at an internal temperature of −20° to −10° C. 68 g of a colorless powder having a melting point of 99° C. and a content of the above compound of 88% [$^{31}$P-NMR: δ(CDCl$_3$)=105.05 ppm] were obtained. Colorless crystals of melting point 112° C. crystallized from acetonitrile. C$_{26}$H$_{29}$Cl$_2$OP calculated: 67.98% C, 6.30% H, 6.74% P (459.397) found: 67.8% C, 6.3% H, 6.8% P 8. Bis-2-methoxyphenylphosphinous acid 2,4-di-tert-butyl ester: inverse addition: a Grignard reagent was prepared from 56.1 g of 2-bromoanisole. This reagent was cooled to −20° C., and a solution of 150 mmol (=46.1 g) of phosphorous acid 2,4-di-tert-butylphenyl ester-dichloride in 120 ml of teter-hydrofuran/n-heptane (1:1) was metered in at an internal temperature of −20° to −10° C. 67 g of colorless crystals having a melting point of 97° C. and a content of 86% of the above compound [$^{31}$P-NMR: δ(CDCl$_3$)=91.14 ppm] were obtained. Colorless crystals of melting point 113° C. crystallized from acetonitrile.

C$_{28}$H$_{35}$O$_3$P calculated: 76.64% C, 7.83% H, 6.87% P (450.56) found: 76.8% C, 7.7% H, 6.9 P.

9. Bis-(4-N,N-dimethylaminophenyl)phosphinousacid2,4-di-tert-butyl ester: inverse addition: a Grignard reagent was prepared from 60.0 g of 4-bromo-N,N-dimethylaniline. This reagent was cooled to −20° C, and a solution of 150 mmol (=46.1 g) of phosphorous acid 2,4-di-tert-butylphenyl ester-dichloride in 120 ml of tetrahydrofuran/n-heptane (1:1) was metered in at an internal temperature of −20° to −10° C. 71 g of colorless crystals having a melting point of 103° C. and a content of 86% of the above compound [$^{31}$P-NMR: δ(CDCl$_3$)=110.41 ppm) were obtained. Colorless crystals of melting point 122° C. crystallized from acetonitrile.

C$_{30}$H$_{41}$N$_2$OP calculated: 75.60% C, 8.67% H, 5.88% N, 6.50% P (432.59) found: 75.5% C, 8.8% H, 5.9% N, 6.6% P.

10. 2,4,6-Trimethylphenyl-2-methoxyphenyl-phosphinous acid 2,4-di-tert-butyl ester
(Method B)
Starting from 29.9 g of 1-bromo-2,4,6-trimethylbenzene and 28.1 g of 4-bromoanisole, 69 g of a pale yellow powder having a softening point of 48° C. and a content of the above compound of 90% [$^{31}$P-NMR: $\delta$(CDCl$_3$)=113.00 ppm] were obtained. C$_{30}$H$_{39}$O$_2$P (462.62)

11. 4-tert-Butylphenyl-l-naphthyl-phosphinous acid 2,4-di-tert-butyl ester (Method B)

Starting from 31.1 g of 1-bromonaphthalene and 32.0 g of 4-tert-butylbromobenzene, 74 g of a pale yellow powder having a softening point of 74° C. and a content of the above compound of 90% [$^{31}$P-NMR: $\delta$(CDCl$_3$): 103.60 ppm] were obtained. C$_{34}$H$_{41}$OP (496.68)

12. 1,4-Naphthalene-bis-[1-naphthyl-phosphinous acid 2,4-di-tert-butylphenyl ester]

(Method B)

Starting from 31.1 g of 1-bromonaphthalene and 21.4 g of 1,4-dibromonaphthalene, 64 g of a pale yellow powder having a softening point of 97% and a content of the above compound of 68% [$^{31}$P-NMR: $\delta$(CDCl b 3)=95.46, 95.83 ppm) were obtained. C$_{58}$H$_{62}$O$_2$P$_2$ (853.08)

13. 1,4-Phenylene-bis-[l-naphthyl-phosphinous acid 2,4-di-tert-butylphenyl ester]

(Method B)

Starting from 31.1 g of 1-bromonaphthalene and 17.7 g of 1,4-dibromobenzene, 60 g of a pale yellow powder having a content of the above compound of 66% [$^{31}$P-NMR: $\delta$(CDCl$_3$)=104.0, 104.12 ppm] were obtained. C$_{43}$H$_{60}$O$_2$(803. 02)

II. Use Examples

The diarylphosphinous acid aryl esters according to the invention listed below were employed f or the experiments.

1. 2,4,6-Trimethylphenyl-phenylphosphinous acid 2,4-di-tert-butylphenyl ester according to Example 1

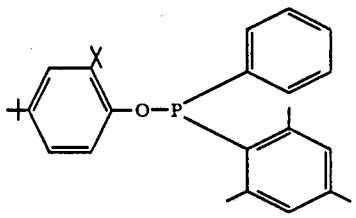

2. 2,4,6-Trimethylphenyl-naphthylphosphinous acid 2,4-di-tert-butylphenyl ester according to Example 2

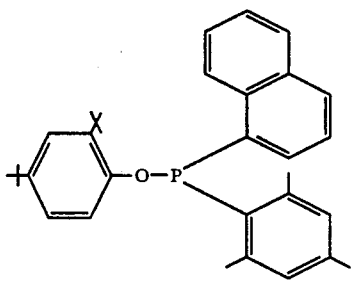

3. Bis-(1-naphthyl)phosphinous acid 2,4-di-tert-butylphenyl ester according to Example 4 or 5.

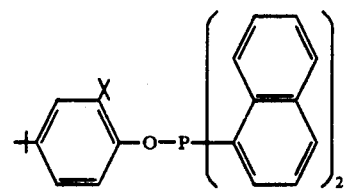

Use Examples 1 to 3 and Comparison Examples A to C 100.0 g of non-stabilized polypropylene powder (density: 0.903 g/cm$^3$; melt flow index MFI 230/5: 4 g/10 minutes) were mixed with 0.1 g of Ca stearate, as an acid acceptor, and the amounts of phosphorus compound which are stated in the tables, and the mixture was extruded several times by means of a laboratory extruder (short compression zone screw, screw diameter 20 mm; length 400 mn, die 30 mm long, 2 mm diameter; speed: 125 revolutions per minute; temperature program: 200°/230°/230° C.) . After the 1st, 5th and 10th pass, samples of the granules were taken and the melt flow index according to DIN 53 735 and the yellowing as the yellowness index according to ASTM D 1925-70 were measured on these samples. Furthermore, injection-molded sheets having the dimensions 60×60×1 mm were produced from the granules of the 1st pass and the yellowing was measured immediately and after storage in heat (7 days at 100° C.).

The results are listed in Tables 1, 2 and 3.

TABLE 1

Effect of phosphorus compounds on the processing stability of polypropylene. Melt flow index MFI 230/5 after several granulations. (MFI in g/10 minutes)

| Example | Phosphorus compound | | MFI after | | |
|---|---|---|---|---|---|
| | | | 1st | 5th | 10th granulation |
| Comparison A | none | | 7.6 | 11.6 | 15.7 |
| Comparison B | 0.1 g | Tris-(2,4-di-t-butyl-phenyl) phosphite | 6.2 | 6.9 | 7.5 |
| Comparison C | 0.1 g | Tetrakis-(2,4-di-t-butylphenyl) 4,4'-biphenylene diphosphonite | 4.3 | 4.6 | 5.5 |
| 1 | 0.1 g | (diarylphosphinous acid aryl ester according to the invention) | 5.5 | 5.0 | 5.8 |
| 2 | 0.1 g | (diarylphosphinous acid aryl ester according to the invention) | 4.9 | 4.8 | 4.5 |
| 3 | 0.1 g | (diarylphosphinous acid aryl ester according to the invention) | 4.6 | 5.1 | 7.4 |

TABLE 2

Color course (yellowness index according to ASTM D 1925-70) during several granulations of polypropylene.

| Example | Phosphorus compound | | YI after | | |
|---|---|---|---|---|---|
| | | | 1st | 5th | 10th granulation |
| Comparison A | none | | 7.5 | 13.4 | 19.7 |
| Comparison B | 0.1 g | Tris-(2,4-di-t-butyl-phenyl) phosphite | 7.5 | 8.9 | 12.8 |
| Comparison C | 0.1 g | Tetrakis-(2,4-di-t-butylphenyl) 4,4'-biphenylene diphosphonite | 6.5 | 6.1 | 8.7 |
| 1 | 0.1 g | (diarylphosphinous acid aryl ester | 5.3 | 6.7 | 9.3 |

TABLE 2-continued

Color course (yellowness index according to ASTM D 1925-70) during several granulations of polypropylene.

| Example | Phosphorus compound | YI after 1st | 5th | 10th granulation |
|---|---|---|---|---|
| 2 | 0.1 g (diarylphosphinous acid aryl ester according to the invention) | 6.2 | 7.7 | 11.0 |
| 3 | 0.1 g (diarylphosphinous acid aryl ester according to the invention) | 5.9 | 7.9 | 11.3 |

TABLE 3

Color course on 1 mm injection-molded sheets immediately after production and after conditioning (7 days at 100° C.)

| Example | Phosphorus compound | YI immediate | after 7 days at 100° C. |
|---|---|---|---|
| Comparison A | none | 2.7 | 6.8 |
| Comparison B | 0.1 g Tris-(2,4-di-t-butyl-phenyl) phosphite | 1.8 | 7.5 |
| Comparison C | 0.1 g Tetrakis-(2,4-di-t-butylphenyl) 4,4'-bi-phenylene diphosphonite | 1.5 | 7.3 |
| 1 | 0.1 g (diarylphosphinous acid aryl ester according to the invention) | 1.8 | 7.8 |
| 2 | 0.1 g (diarylphosphinous acid aryl ester according to the invention) | 1.9 | 7.7 |
| 3 | 0.1 g (diarylphosphinous acid aryl ester according to the invention) | 1.5 | 7.3 |

What is claimed is:

1. A plastic molding composition consisting essentially of
   a) as a thermoplastic or a thermosetting plastic, a polymer containing polymerized mono-olefin or di-olefin units or combinations thereof and
   b) a diarylphosphinous acid aryl ester of the formula (I)

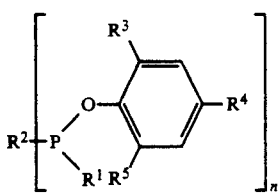

(I)

in a ratio of (90 to 99.99): (0.01 to 10), where n=1 or 2, in which $R^1$ and $R^2$ independently of one another, as monovalent radicals, are a phenyl or naphthyl radical, each of which carries at least 1 and up to 5 substituents, in which the substituents are identical or different and are a nonaromatic hydrocarbon radical, an alkoxy radical, alkylthio radical or dialkylamino radical having in each case 1 to 8 carbon atoms, aryl or aryloxy having in each case 6 to 10 carbon atoms or halogen having an atomic number of 9 to 35, and
$R^2$, as a divalent radical, is a phenylene or biphenylene radical, which is unsubstituted or substituted by up to 4 nonaromatic hydrocarbon radicals having 1 to 8 carbon atoms, or a naphthylene radical, which is unsubstituted or carries 1 to 4 nonaromatic hydrocarbon radicals having 1 to 8 carbon atoms as substituents, and $R^3$, $R^4$ and $R^5$ independently of one another are hydrogen or a branched or unbranched hydrocarbon radical having 1 to 8 carbon atoms.

2. The plastics molding composition as claimed in claim 1, wherein the plastic is a poly-mono-olefin.

3. The plastics molding composition in claim 1, wherein the plastic is a polypropylene.

4. The plastics molding composition as claimed in claim 1, which consists essentially of
   a) the thermoplastic or the thermosetting plastic,
   b) the diarylphosphinous acid aryl ester mentioned and
   c) an ester of c1) 3,3-bis-(3'-t-butyl-4'-hydroxy-phenyl)-butanoic acid of the formula (III)

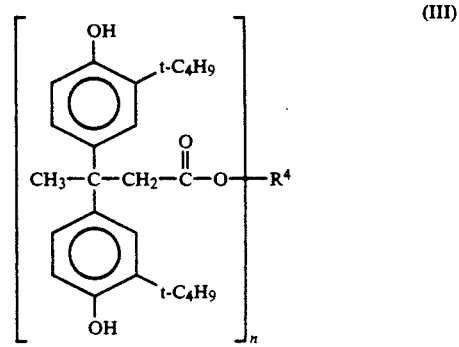

(III)

in which n is 1 or 2 and $R^4$ is a $C_1$ to $C_{18}$-alkyl radical, if n is 1, or is a $C_1$ to $C_{12}$-alkylene radical, if n is 2, or c2) β-(3,5-di-t-butyl-4-hydroxy-phenyl)-propionic acid of the formula (IV)

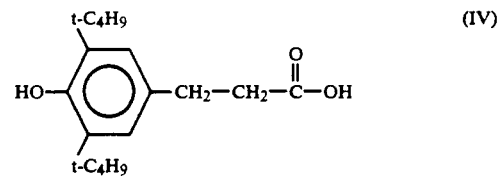

(IV)

with a mono- to tetrahydric alcohol in a ratio of a:b:c of (90 to 99.98): (0.01 to 5): (0.01 to 5) % by weight.

5. The plastics molding composition as claimed in claim 4, which consists essentially of
   a) the thermoplastic or the thermosetting plastic,
   b) the diarylldhosphinous acid aryl ester mentioned and
   c) an ester of c1) 3,3-bis-(3'-t-butyl-4'-hydroxy-phenyl)-butanoic acid of the formula III in which n is 1 or 2 and $R^4$ is a $C_1$ to $C_{18}$-alkyl radical, if n is 1, or is a $C_1$ to $C_{12}$-alkylene radical, if n is 2, or c2) β-(3,5-di-t-butyl-4-hydroxy-phenyl)-propionic acid of the formula (IV) with a mono- to tetrahydric alcohol in a ratio of a:b:c of (98 to 99.95): (0.025 to 1): (0.025 to 1).

6. The plastics molding composition as claimed in claim 1, which additionally consists essentially of antioxidants, UV absorbers, light stabilizers, metal deactivators, peroxide-destroying compounds, basic costabilizers, nucleating agents, fillers, reinforcing agents, plasticizers, lubricants, emulsifiers, pigments, optical brighteners, flameproofing agents, antistatics or blowing agents.

7. A diarylphosphinous acid aryl ester of the formula (I)

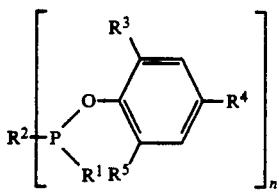

where n=1 or 2, in which $R^1$ and $R^2$ independently of one another, as monovalent radicals, are a phenyl or naphthyl radical, each of which can carry 1 to 5 substituents, in which the substituents are identical or different and are a nonaromatic hydrocarbon radical, an alkoxy radical, alkylthio radical or dialkylamino radical having in each case 1 to 8 carbon atoms, aryl or aryloxy having in each case 6 to 10 carbon atoms or halogen having an atomic number of 9 to 35, and $R^2$, as a divalent radical, is a phenylene or biphenylene radical, which is unsubstituted or substituted by up to 4 nonaromatic hydrocarbon radicals having 1 to 8 carbon atoms, or a naphthylene radical, which is unsubstituted or carries 1 to 4 nonaromatic hydrocarbon radicals having 1 to 8 carbon atoms as substituents, and $R^3$ and $R^4$ are a tert.-butyl radical, and $R^5$ is hydrogen or a branched or unbranched hydrocarbon radical having 1 to 8 carbon atoms.

8. The method of stabilizing a thermoplastic or thermosetting plastic polymer containing polymerized mono-olefin or diolefin units or combinations thereof with a compound of the formula (I) as defined in claim 7, by itself or in combination with a phenolic antioxidant, which comprises: incorporating said compound of the formula (I), by itself or in combination with a phenolic antioxidant, into the polymer.

* * * * *

UNITED STATES PATENT AND TRADEMARK OFFICE
CERTIFICATE OF CORRECTION

PATENT NO. : 5,281,640
DATED : January 25, 1994
INVENTOR(S) : Dieter Regnat, et al It is certified that error appears in the above-indentified patent and that said Letters Patent is hereby corrected as shown below:

In claim 1, column 17, (line 42) "plastic" should read --plastics--.

In claim 5, column 18, line 59, "diarylldhosphinous" should read --diarylphosphinous--.

In claim 5, column 18, line 63, "$C_1$to" should read --$C_1$ to--.

Signed and Sealed this

Fifteenth Day of November, 1994

Attest:

BRUCE LEHMAN

*Attesting Officer*  *Commissioner of Patents and Trademarks*